(12) United States Patent
Miller

(10) Patent No.: US 8,744,983 B2
(45) Date of Patent: Jun. 3, 2014

(54) CLUSTER ANALYSIS SYSTEM AND METHOD TO IMPROVE SORTING PERFORMANCE

(75) Inventor: Lucas R. Miller, Albuquerque, NM (US)

(73) Assignee: Illinois Tool Works Inc., Glenview, IL (US)

( * ) Notice: Subject to any disclaimer, the term of this patent is extended or adjusted under 35 U.S.C. 154(b) by 249 days.

(21) Appl. No.: 13/510,649

(22) PCT Filed: Nov. 15, 2010

(86) PCT No.: PCT/US2010/056697
§ 371 (c)(1),
(2), (4) Date: May 18, 2012

(87) PCT Pub. No.: WO2011/062866
PCT Pub. Date: May 26, 2011

(65) Prior Publication Data
US 2012/0233101 A1   Sep. 13, 2012

Related U.S. Application Data

(60) Provisional application No. 61/262,775, filed on Nov. 19, 2009.

(51) Int. Cl.
*G06F 15/18* (2006.01)

(52) U.S. Cl.
USPC .......................................................... 706/12

(58) Field of Classification Search
CPC combination set(s) only.
See application file for complete search history.

(56) References Cited

U.S. PATENT DOCUMENTS

| | | | |
|---|---|---|---|
| 5,062,296 A | 11/1991 | Migliori | |
| 5,425,272 A | 6/1995 | Rhodes et al. | |
| 5,591,913 A | 1/1997 | Tucker | |
| 7,132,652 B1 | 11/2006 | Testoni | |
| 8,295,315 B2 * | 10/2012 | Ward et al. ...................... | 372/20 |

FOREIGN PATENT DOCUMENTS

DE         4207728 A1     9/1993

OTHER PUBLICATIONS

Jim Schwarz et al., "Process Compensated Resonant Testing in Manufacturing Process Control," Materials Evaluation, May 1, 2005, pp. 736-739.

(Continued)

*Primary Examiner* — Michael B Holmes
(74) *Attorney, Agent, or Firm* — Mark W. Croll; Paul F. Donovan

(57) ABSTRACT

A method for classifying an unknown part includes acquiring a broadband frequency response for a plurality of parts in a training set of parts, the training set of parts including a plurality of non-flawed parts and a plurality of flawed parts, performing a statistical analysis on the broadband frequency responses to form a plurality of part subsets, the plurality of part subsets including at least one subset of non-flawed parts and at least one subset of flawed parts, and utilizing the plurality of part subsets to form a blended subset of parts, the blended subset of parts being used to classify an unknown part as either a defective part or a non-defective part. A tool for implementing the method is also described.

20 Claims, 5 Drawing Sheets

(56) References Cited

OTHER PUBLICATIONS

Yu-Hsiang Hsiao et al., "Multiclass MTS for Saxophone Timbre Quality Inspection Using Waveform-shape-based Features," IEEE Transactions on Systems, Man, and Cybernetics—Part B: Cybernetics, vol. 39, No. 3, Jun. 2009, pp. 690-704.

Chao-Ton Su et al., "Multiclass MTS for Simultaneous Feature Selection and Classification," IEEE Transactions on Knowledge and Data Engineering, vol. 21, No. 2, Feb. 2009, pp. 192-205.

ISR for PCT/US2010/056697 dated Mar. 14, 2011.

* cited by examiner

CLUSTER ANALYSIS SYSTEM AND METHOD TO IMPROVE SORTING PERFORMANCE

CROSS REFERENCE TO RELATED APPLICATION

This Non-Provisional Application is national phase of PCT/US2010/056697 filed Nov. 15, 2010, and claims benefit to U.S. Provisional Application Ser. No. 61/262,775 filed on Nov. 19, 2009.

BACKGROUND OF THE INVENTION

The present invention relates generally to pattern recognition systems, and more particularly to, a system and method for improving sorting performance of various parts using cluster analysis.

Various parts are utilized by customers to fabricate more complex assemblies. Customers utilize various testing methods to identify both "good" and "bad" parts prior to the parts being installed into the more complex assembly. The good parts conform to the manufacturer's specifications. Whereas, the bad parts do not conform to the customers specifications.

To identify both the good parts and the bad parts, the customer typically provides an outside testing facility, for example, with a set of known good and bad parts. The set of known good and bad parts is referred to herein as a "training set". The testing facility utilizes a conventional system to collect various data on the training set. The data is then stored in a database in the conventional system. The data collected for each part includes the frequency of a resonance or peak, and the values for that peak, such as amplitude, zero-crossing width, etc. The resultant frequency values for all of the selected peaks are then transmitted to a conventional statistical analysis/pattern recognition (VIPR) tool.

The VIPR tool utilizes the resultant frequencies to identify a Mahalanobis Taguchi System/Mahalanobis Distance (MTS). The MTS Distance is used to identify a subset of frequencies that can be used to find a difference between the provided good and bad parts and optimize a threshold distance to accept as many good parts as possible and reject as many bad parts as possible. This initial MTS test uses only the good parts to create its test and then assigns an "MTS distance" for every part (including the bad parts), which is the distance the part is from the "center" of the good parts.

The MTS Distance is a multi-dimensional value that may be represented as an ellipse in a two-dimensional (2D) figure and as an "egg-shape" in a three-dimensional (3D) figure, with all parts inside the "egg" passing the MTS test (the good parts) and all of the parts outside the "egg" failing the MTS test (the bad parts). Typically 3-7 frequencies (dimensions) are used by the MTS test to identify the good and bad parts. In the case that some bad parts are accepted, an additional "bias test" may be used to reject these additional bad parts. The bias test is performed by calculating an additional MTS distance, using the frequencies for only the bad parts. As a result, two MTS distances are calculated for each part, the distance the part is from the "goods center ellipsoid" and the distance the part is from the "bads center ellipsoid." A ratio of the two MTS distances is used to reject additional parts. More generally, if conventional system determines that the part is closer to the center of the bads center ellipsoid, the part is more likely to be a bad or non-conforming part, and is rejected. The VIPR then returns a list of possible solutions that may include the 3-7 frequencies used to distinguish the good parts from the bad parts. The possible set of solutions is referred to as a "VIPR Score." The VIPR score is a sum of the probabilities of good parts passing and bad parts failing the MTS and Bias tests.

A conventional validation tool utilizes the VIPR score to ensure that all of the above described peaks can be selected properly and also ensure that there are no conflicts or problems with the VIPR solution. The validation tool determines which peaks may be used to predict a window to look for the next peak and organizes the order that the peaks are swept in an optimal way. Each potential sort is given a Validation score that is the sum of the probabilities that the good parts will pass the tests and the bad parts will fail the tests with real data, not just frequencies. A user inputs the solution "into production", meaning that the solution is used on unknown parts received from new production. When the customer's process changes or the results are no longer acceptable data is taken on new, classified parts, and the whole process is repeated.

However, the conventional VIPR system is generally less effective when processing parts having a large process variation. More specifically, the variation in the good parts becomes so large that the variation obscures the differences between the good and bad parts. Therefore, VIPR is forced to group all of these good parts, which may not be that similar, into one large group. Because VIPR utilizes a single large group to identify the good parts, the boundary for the large group may become so large that bad parts may be inadvertently included in the grouping of good parts.

BRIEF DESCRIPTION OF THE INVENTION

In one embodiment, a method for classifying an unknown part is provided. The method includes acquiring a broadband frequency response for a plurality of parts in a training set of parts, the training set of parts including a plurality of non-flawed parts and a plurality of flawed parts, performing a statistical analysis on the broadband frequency responses to form a plurality of part subsets, the plurality of part subsets including at least one subset of non-flawed parts and at least one subset of flawed parts, and utilizing the plurality of part subsets to form a blended subset of parts, the blended subset of parts being used to classify an unknown part as either a defective part or a non-defective part.

In another embodiment, a cluster analysis tool is provided. The cluster analysis tool includes an ultrasound probe for scanning a training set of parts, the training set of parts including a plurality of non-flawed parts and a plurality of flawed parts to, and a cluster analysis module coupled to the ultrasound probe. The cluster analysis module is configured to acquire a broadband frequency response from the ultrasound probe for a plurality of parts in a training set of parts, the training set of parts including a plurality of non-flawed parts and a plurality of flawed parts, perform a statistical analysis on the broadband frequency responses to form a plurality of part subsets, the plurality of part subsets including at least one subset of non-flawed parts and at least one subset of flawed parts, and transmit the plurality of part subsets to a statistical analysis tool, the statistical analysis tool forming a blended subset of parts, the blended subset of parts being used to classify an unknown part as either a defective part or a non-defective part.

Other features and advantages of the invention will become apparent to those skilled in the art upon review of the following detailed description, claims and drawings in which like numerals are used to designate like features.

Figure 1:
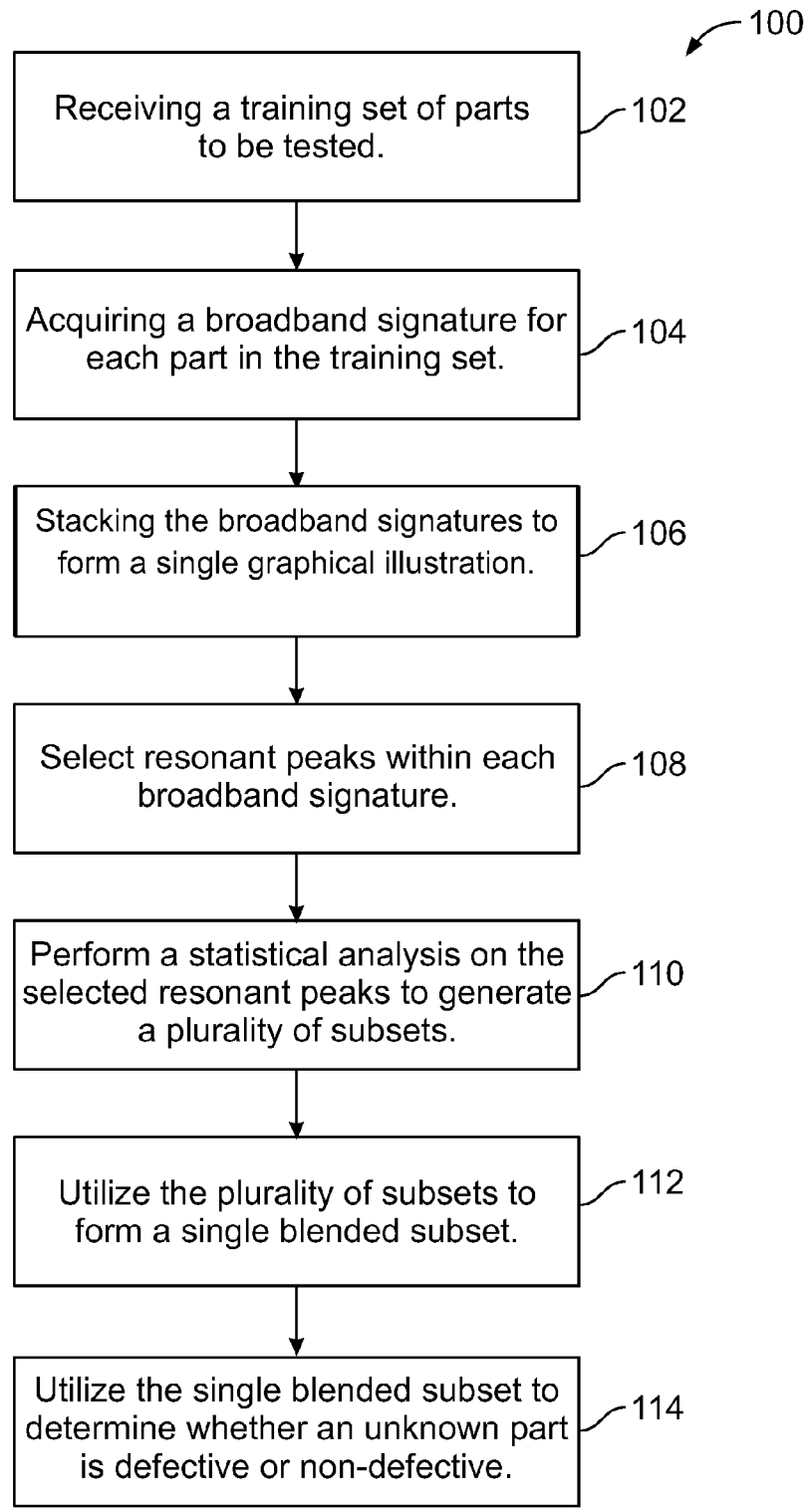
FIG. 1 is a flowchart of an exemplary method of classifying an unknown part.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE INVENTION

Described herein is a cluster analysis method and apparatus to facilitate classifying an unknown part as either a defective part or a non-defective part. The method also determines the type of defect when the part is classified as a defective part. The method utilizes a training set of parts to form a plurality of subsets, also referred to herein as clusters or parts clusters. The cluster analysis method described herein may be used as preprocessor to a statistical analysis/pattern recognition tool, such as, for example, the VIPR system described above to improve the results of the statistical analysis/pattern recognition (VIPR) tool. As used herein, cluster analysis is a class of algorithms that assign observations from a large group into at least one smaller subset or cluster. The advantage of identifying the quantity of groups of parts, and which parts belong to which cluster, improves the statistical analysis/pattern recognition tool result. Advantages of the cluster analysis method described herein include correlating clusters with known groupings without utilizing prior knowledge of the groupings. The cluster analysis method described herein enables the statistical analysis/pattern recognition tool to create two or more subsets or clusters that are grouped more tightly. The smaller subsets enhance the ability of the statistical analysis/pattern recognition tool to accept all of the non-defective parts and reject all the defective parts.

FIG. 1 is a flowchart illustrating an exemplary method 100 of classifying an unknown part as either a defective part or a non-defective part. The method 100 includes receiving 102 a training set of parts to be tested. The training set includes a quantity of known non-defective and defective parts. At step 104, a broadband signature is acquired for each part in the training set. In the exemplary embodiment, each of the parts in the training set is scanned using an ultrasound signal to acquire a broadband signature for each part. An ultrasound probe, having a plurality of ultrasound transducers (shown below) receives echoes from each part to generate the broadband signature of the part. The broadband signature includes the resonant peaks and valleys of the frequency response received at the ultrasound transducers. In the exemplary embodiment, each of the parts in the training set is scanned at a plurality of frequencies to generate the broadband signature for each part.

To generate the broadband signature for each part in the training set, each part is scanned with acoustic waves that are generated by a transceiver through the ultrasound probe. In the exemplary embodiment, acoustic waves having a predetermined frequency range are applied to the part. The response of the part to the acoustic waves is sensed at a plurality of sensor locations. The acoustic waves may be applied to the part in a series of step increases in frequency and at intervals in frequency much less than the width of the resonance and at intervals in time much less than the time required for the resonance to decay after excitation at a fixed frequency. For example, the frequency of the acoustics wave may initially be set to 1 Hertz (Hz), referred to herein as a start frequency, or any other frequency selected for the measurement. Moreover, the frequency step may be selected by determining the start frequency and a stop frequency, and then dividing the frequency difference by the number of steps desired for the measurement. For example, a measurement from a start frequency of 1 Hz to a stop frequency of 1 kHz requiring 100 steps will result in a 10 Hz step.

The broadband signature, i.e., the frequency response is then recorded. Recording may be of at least one resonant response (the frequency of at least one resonant response and its magnitude). Resonance and resonant response, as used herein, refer to the total response which may be described as the frequency, the width in frequency, and the amplitude. The resonant frequency may be at frequencies which are dependant upon dimensions of the part and dependant upon the stiffness of the part. For example, a first resonant frequency may be dependant upon dimensions of the part and a second resonant frequency may be dependant upon the stiffness of the part.

Figure 2:
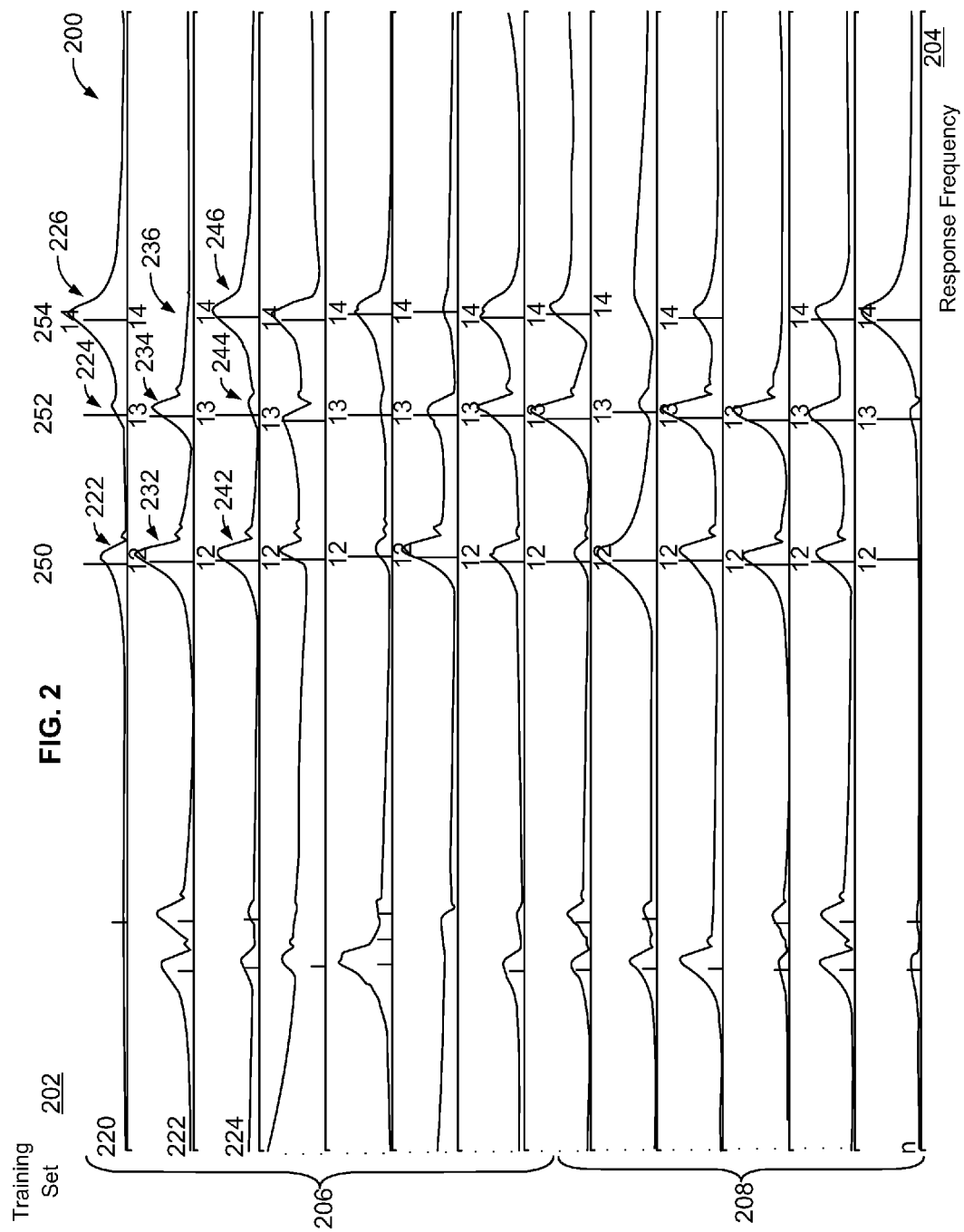
FIG. 2 is a graphical illustration of exemplary broadband signatures acquired in accordance with various embodiments.

At 106, the broadband signatures acquired for each part in the training set are stacked to form a single graphical illustration. The graphical illustration includes a plurality of frequency responses 200, i.e. broadband signatures, acquired for each part in an exemplary training set 202. For example, FIG. 2 is a graphical illustration of the exemplary frequency responses 200 acquired at step 104 where the Y-axis represents parts the exemplary training set 202 and the X-axis represents the frequency response 204 recorded for each part in the training set 202 at step 104. As shown in FIG. 2, in the exemplary embodiment, the exemplary training set 202 includes 13 parts to be tested. As discussed above, the training set 202 includes a quantity of known non-defective and defective parts. In the exemplary embodiment described herein, the training set 202 includes 7 known non-defective parts 206 and 6 known defective parts 208. However, it should be realized that the training set 202 may include any quantity of known non-defective parts 206 and known defective parts 208.

Referring again to FIG. 1, at 108, resonant peaks within each broadband frequency response shown in FIG. 2 are selected for each part in the training set 202. In the exemplary embodiment, the resonant peaks represent a resonance where the part vibrates at that frequency. It should be realized that all the non-defective and defective parts in the training set 202 have peaks that occur at various resonances. In one embodiment, a computer (shown below), select resonant peaks using the frequency responses 202 and the stacking arrangement shown in FIG. 2 enables an operator to visually verify the selected resonant peaks or to modify the computer's selection of resonant peaks. However, it should be realized that the computer may automatically implement the method described herein, in which case the graphical illustration shown in FIG. 2 is not utilized.

Accordingly, in the exemplary embodiment, resonant peaks are identified for each part in the training set 202. The resonant peaks are then collated to identify parts that have peaks in common, e.g. parts that have a resonance that occurs at the same, or substantially the same frequency. For example, a first part 220 has a plurality of peaks 222, 224, and 226 that each occur at a different frequency. A second part 230 has a plurality of peaks 232, 234, and 236 that each occur at a different frequency. A third part 240 has a plurality of peaks 242, 244, and 246 that each occur at a different frequency, etc. As shown in FIG. 2, the frequency response, or peak 222 for the first part 220 occurs at substantially the same frequency as the frequency response 232 for the second part 230 and the frequency response 242 for the third part 240. Moreover, at least some of the n parts has a frequency response or peak that occurs near, or within a predetermined distance, as at least some of the same locations as the peaks 222, 224, and 226, etc.

Thus, in the exemplary embodiment, the broadband frequency responses for each of the parts in the training set 202 are used to identify columns, where each column represents a plurality of parts in the training set that each generated a frequency response at substantially the same frequency. For example, a first column 250 represents information generated by each part in the training set 202 at a first frequency. The first column 250 shows that the majority of the parts in the training set 202 had a frequency response at the first frequency. A second column 252 represents information generated by each part in the training set 202 at a different second frequency, and a third column 254 represents information generated by each part in the training set 202 at a third frequency. Thus, the columns are used to identify frequency responses that are common to most, if not all, the parts in the training set 202. It should be realized that although FIG. 2 illustrates three columns 250, 252, and 254, that the response information may be sorted into more than, or fewer than, three columns. In one embodiment, a computer may automatically define the columns. An operator may then accept the defined columns, remove columns, add additional columns, etc. Optionally, an operator may manually select the columns.

Referring again to FIG. 1, at 110 a statistical analysis is performed on the columns identified at 110 to form a plurality of part subsets. Specifically, the information in the columns identified at 110 is used to assign the parts in the training set 202 into smaller subsets or clusters. The part subsets, or clusters, include at least one subset having only non-defective parts and at least one second subset having only defective parts. In the exemplary embodiment, the columns identified at 110 may be used to form a plurality of subsets of known non-defective parts and a plurality of subsets that include known defective parts as is discussed in more detail below.

Performing a statistical analysis may include, for example, utilizing an algorithm to generate a signature or characterize the parts such as the resonant frequencies, a sum of resonant frequencies, a difference in resonant frequencies, and/or any other manipulations of the columns which may be used to generate statistical information from the data. In the exemplary embodiment, the statistical analysis groups the non-defective parts into subsets by utilizing the statistical analysis to identify a center for each subset and then determining a distance for each part from the center of the subset. For example, the algorithm initially performs the statistical analysis by inputting an initial value or guess that represents a center of for each subgroup. For example, assuming that the subsets includes two non-defective parts subsets and two defective parts subsets, an initial estimate for the center of each of the four subsets is first entered. Each part in the training set 202 is then assigned a membership grade that represents how close that part is to the center of each group.

For example, each non-defective part is assigned a grade based on how far that specific non-defective part is from the center of each of the two non-defective part subsets. Moreover, each defective part is assigned a grade based on how far that specific defective part is from the center of each of the two defective part subsets. The centers for each of the subsets is then iteratively updated based on the membership grades assigned to each part in the subset. In operation, the iteration is utilized to minimize an objective function that represents the distance from any given part to a group center weighted by that part's membership grade. In general, the algorithm is utilized to group the parts into subsets of non-defective parts and defective parts. Moreover, the algorithm also forms multiple subsets of non-defective parts and multiple subsets of defective parts based on the scoring described above. As a result, membership, i.e. which part belongs in which specific subset, is determined by calculating a distance for each part from the center of a subset, the smaller the distance the more likely a part belongs to that group. Specifically, the algorithm determines the distance for each part to the center of the first and second subgroups.

Figure 3:
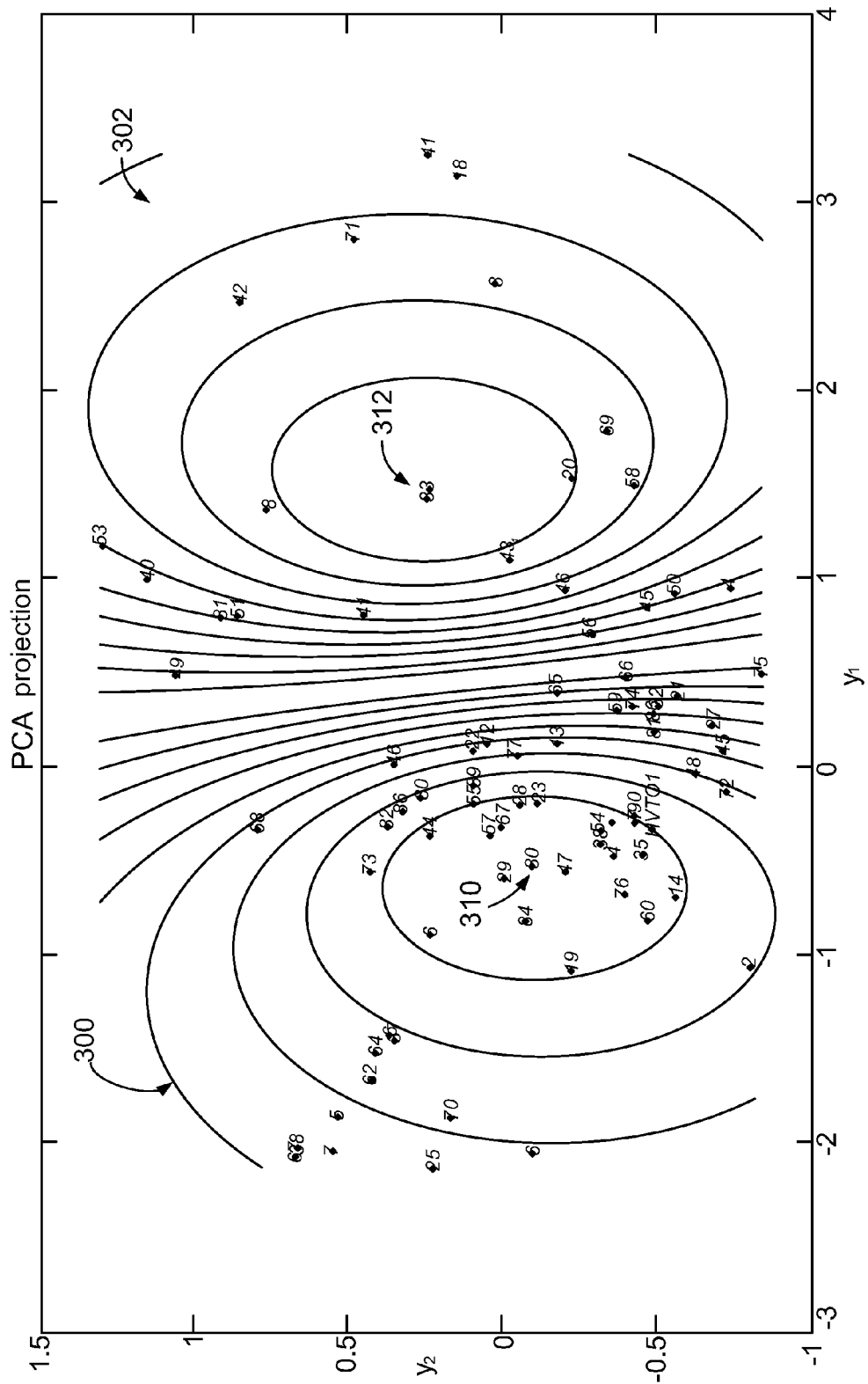
FIG. 3 is a graphical illustration of an exemplary distribution of parts sorted into two exemplary subsets in accordance with various embodiments.

FIG. 3 is a graphical illustration of an exemplary distribution of parts sorted into two exemplary subsets 300 and 302 using the algorithm discussed above. In this example, the subsets 300 and 302 represent two subsets of non-defective parts from the training set 202. As shown in FIG. 3, subset 300 has a center 310 that is determined as discussed above. Additionally, subset 302 has a center 312. In this example, approximately 80 non-defective parts, numbered 1-80 have been sorted into the two non-defective parts subsets 300 and 302. Each dot, and corresponding part number located adjacent each dot, represents the location of one of the non-defective parts and also the distance of each non-defective part from the centers 310 and 312, respectively. As discussed above, each part is preferably placed in a subset that minimizes a distance between that part and a center of the subset. Accordingly, subset 300 may have a first quantity of parts and subset 302 may have a different quantity of parts. For example, subset 300 may have 20 non-defective parts and subset 302 may have 10 non-defective parts. This same procedure discussed above is also applied to the set of defective parts to place the defective parts into respective subsets. It should be realized that the subsets of non-defective parts include only non-defective parts, whereas the subsets of defective parts include only defective parts.

Referring again to FIG. 1, at 112 the subsets generated at 110 are input to a statistical analysis/pattern recognition tool to form a single subset of parts, referred to herein as the blended subset, that may be used to test an unknown part to determine if the unknown part is a non-defective part or a defective part. In the exemplar embodiment, the subsets formed above are transmitted individually to the statistical analysis/pattern recognition tool. For example, assume that the first subset 300 of non-defective parts is input to the statistical analysis/pattern recognition tool, the statistical analysis/pattern recognition tool then compares each of the parts in the subset 300 to each of the defective parts located in the defective parts subsets to identify resonant peaks to enable the tool to distinguish between the non-defective parts and the defective parts when testing an unknown part. The second subset 302 of non-defective parts is then input to the statistical analysis/pattern recognition tool. As discussed above, the statistical analysis/pattern recognition tool then compares each of the parts in the subset 302 to each of the defective parts located in the defective parts subsets to identify resonant peaks to enable the tool to distinguish between the non-defective parts and the defective parts when testing an unknown part.

It should be realized that the statistical analysis/pattern recognition tool may use other different comparisons to form the blended subset. For example, the statistical analysis/pattern recognition tool may compare the first subset 300 of non-defective parts to a first subset of defective parts, compare the first subset 300 of non-defective parts to a second subset of defective parts, compare the second subset 302 of non-defective parts to the first subset of defective parts; and/or compare the second subset 302 of non-defective parts to the second subset of defective parts. In the exemplary embodiment, utilizing multiple subsets of defective parts enables the statistical analysis/pattern recognition tool to identify the exact subset to which an unknown part should be included. For example, a first subset of defective parts may include parts having a crack. A second subset of defective parts may include parts having a dimensional defect such as shrinkage, perocity, mass, and/or stiffness. Thus, the improved sorting ability described above, enables an operator to determine whether an unknown part has a crack or some other defect.

Referring again to FIG. 1, at 114 the statistical analysis/pattern recognition tool utilizes the single blended subset to test unknown parts. In the exemplary embodiment, the single blended subset may include 2 to 9 different resonant response frequencies that may be utilized to determine whether an unknown part is either a defective part or a non-defective part. Further, if the unknown part is classified as a defective part, the single blended subset enables the part to be assigned to a specific subset of defective parts, where each subset represents a different flaw. Thus, the method not only determines whether an unknown part is defective or not, the method also enables the operator to identify the specific part defect. In the exemplary embodiment, the method 100 described above may be repeated until the operator receives new parts to further train the statistical analysis/pattern recognition tool. For example, when a new unknown part is received, the method 100 again sorts the part into one of the subsets or clusters that include subsets of non-defective parts and subsets of defective parts. Repeating the method enables the tool to verify the classification of the newly added part. The tool then identifies whether the new part is either a non-defective part or a defective part. Moreover, if the tool disagrees with a user's classification of the part, the tool may generate a visual or audio indication to alert the user to perform some additional action prior to the part being analyzed by tool. In the case that some defective parts in the training set 200 are inadvertently classified as non-defective parts, the method 100 may also implement a "bias test" to reject these additional defective parts.

Figure 4:
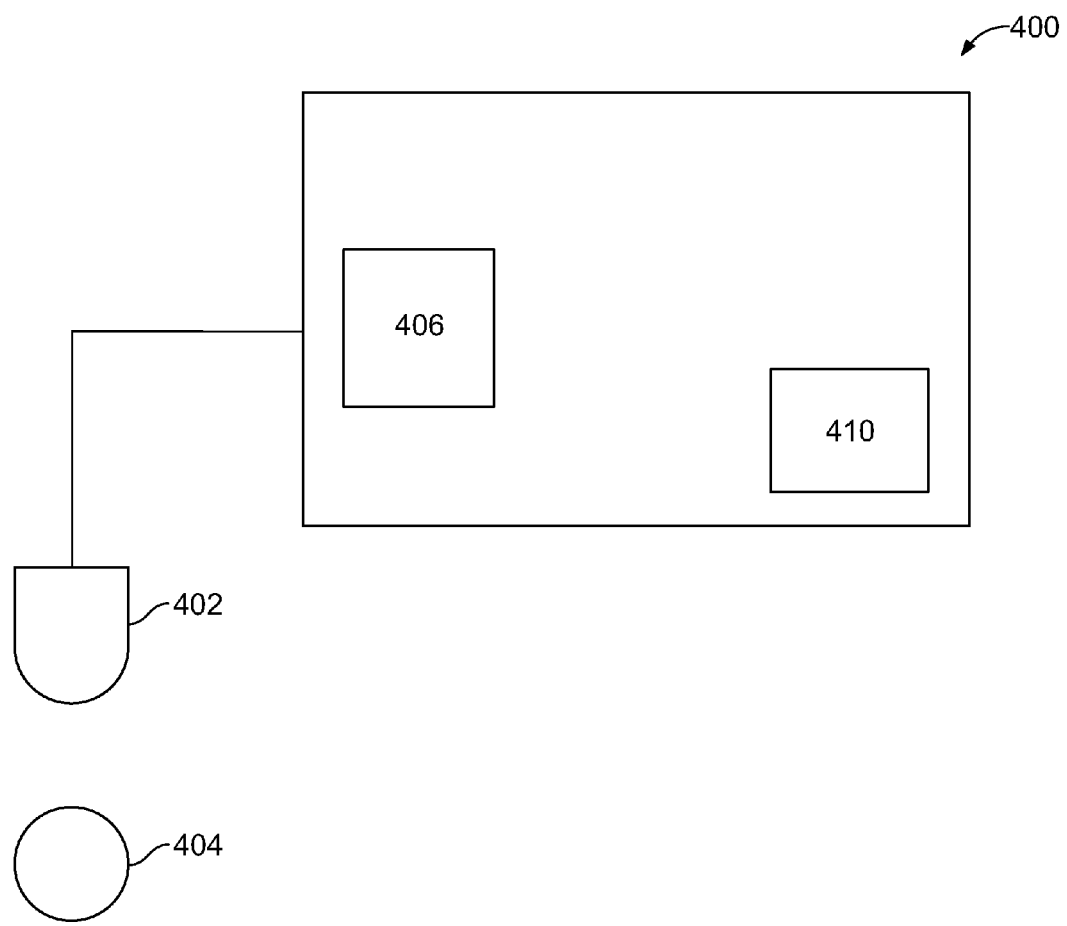
FIG. 4 is a simplified block diagram of an exemplary tool that may be utilized to implement the method shown in FIG. 1 in accordance with various embodiments.

Various embodiments of the method described herein may be performed by, or used with, a cluster analysis tool 400 shown in FIG. 4. It should also be realized that although FIG. 4 illustrates an exemplary cluster analysis tool 400 that is embodied as an ultrasound imaging system, the method 100 may be performed using any system that is configured to perform the cluster analysis method described herein and the cluster analysis tool 400 represents an embodiment of one such system. In the exemplary embodiment, the cluster analysis tool 400 includes an ultrasound probe 402 that is configured to scan various parts 404, such as the parts in the training set 202 described above. In operation, the ultrasound system probe 402 is configured to induce an ultrasound signal into each part 404. At least one ultrasound transducer 406 receives responses from the part 404 to generate a broadband signature of the part 404. The broadband signature includes the resonant peaks and valleys of the ultrasound response received at the ultrasound transducer 406. In the exemplary embodiment, each part is scanned at a plurality of frequencies to generate the broadband signature for each part. Moreover, a broadband signature is acquired for each part in a training set of parts as discussed above.

In the exemplary embodiment, the cluster analysis tool 400 also includes a cluster analysis module 410 that is configured to perform the methods described herein. Specifically, the method 100 may be implemented as a set of instructions on the cluster analysis module 410. Optionally, the cluster analysis module 410 may be hardwired or fabricated to perform the method 100. In operation, the cluster analysis module 410 is configured to identify parts from the same mold, determine whether parts from the same mold are non-defective or defective parts, and/or identify similar defects in a plurality of parts and then assign the parts having similar defects to the same cluster. The defects may include, for example, nodules, inclusions, hardening, non-uniformity, co-molding, etc. In the exemplary embodiment, parts having similar ultrasound based frequency response are assigned to the same cluster.

Figure 5:
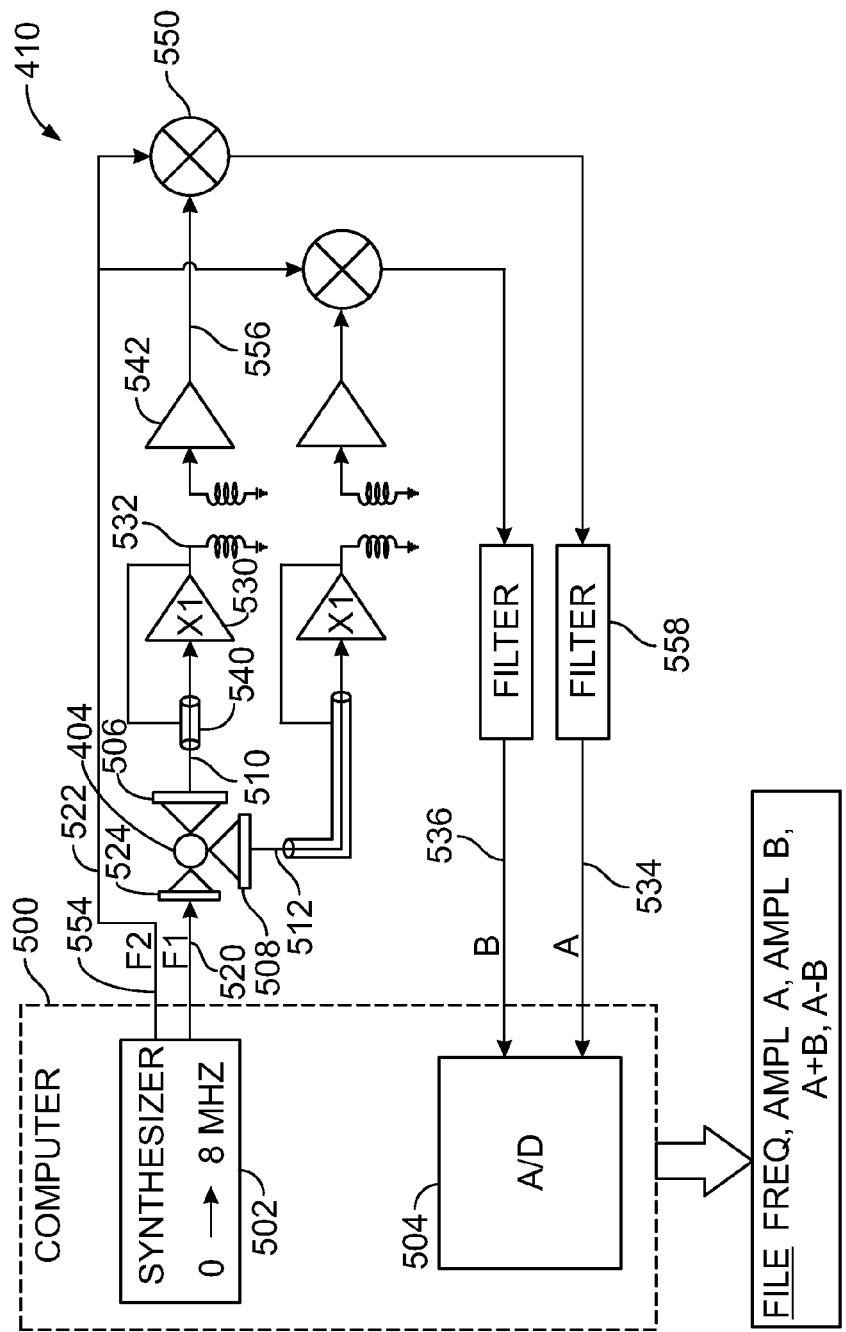
FIG. 5 is a simplified schematic illustration of a portion of the tool shown in FIG. 4 in accordance with various embodiments.

FIG. 5 is a schematic illustration of the exemplary cluster analysis module 410 shown in FIG. 4 for performing resonant ultrasound spectroscopy measurement. In one embodiment, the module 410 includes a computer 500. Optionally, the computer 500 may be formed as part of the cluster analysis tool 400. In operation the computer 500 controls the operation of a synthesizer 502 and a 16 bit analog to digital converter 504 for each data input channel connected to each receiving transducer 506, 508. The transducer 506 has an output on line 510 and the transducer 508 has an output on line 512.

The synthesizer 502 preferably has a frequency range from greater than 0 to 8 mHz. In operation, the synthesizer 502 provides two outputs which are the frequency F1 at output 520 and a second output which is the frequency F2 which is either F1 plus a constant frequency such as 1000 Hz for heterodyne operation of the receiver, or at F1 for homodyne operation, at line 522. A first transducer 524 is excited at the frequency F1 by the synthesizer 502. The transducer 524 provides ultrasonic vibration to an object, such as the part 404 to be tested.

The response of the part 404 is then received by the two separate output transducers 506 and 508. The circuitry from the output transducer 506 and the A/D converter 504 can be identical to circuitry between the transducer 508 and the A/D converter 504. For this reason, only the circuitry between transducer 506 and A/D converter 504 are discussed below. A times one (×1) amplifier 530 is connected to the transducer 506 and provides current for a transformer 532. The output from the transducer 506 is connected to a receiver (not shown) that provides amplification and noise rejection in the circuit between the transducer 506 and the A/D converter 504.

An output A (line 534) is applied to an A/D converter 504 within the computer. Typically, the A/D converter 504 includes a 16 bit A/D conversion for each of lines 534 and 536. The converted information is then entered into a file which includes the measured frequency response information, the amplitude of A, the amplitude of B, the amplitude of A plus B, and the amplitude of A minus B. This file is then used for further analysis of the spectrum to determine characteristics of the part 404 being tested as discussed above in method 100. The times one (×1) amplifier 530 provides feedback to an inner coaxial cable shield 540 which surround the lead from the transducer 506 to the amplifier 530. The shield 540 is another grounded shield which can also be used for noise suppression.

In the exemplary embodiment, the transformer 532 is a 4:1 step down transformer used for impedance matching to the input of an amplifier 542. In this regard, it should be noted that the output impedance of the amplifier 530 is much lower than the output impedance of the transducer 506. This provides for the power gain and the necessary feedback to the shield 540. The amplifier 542 may have a gain factor of 100:1 or a 40 db gain. The amplifier 542 may be implemented as a broadband amplifier having a band pass on the order of 50 mHz, for example.

The cluster analysis module 410 may also include a mixer 550 that has an output which may be, for example, a 1 kHz signal having a magnitude which is proportional to the magnitude of the frequency F1 provided on line 520 from the synthesizer 502. The function of the synthesizer 502 is to provide a point-by-point multiplication of instantaneous values of inputs on lines 554 and 556. The mixer 550 also has many high frequency output components which are of no interest. The high frequency components are therefore filtered out by a low-band pass filter 558. The filter 558 serves to clean-up the signal from the mixer 550 and also provides a voltage on line 534 which is only the 1 kHz signal at an amplitude which is proportional to the amplitude of the output 510 of the transducer 506.

Described herein is an exemplary method that may be used as a preprocessor to an exemplary statistical analysis/pattern recognition tool such as VIPR, for example. In operation, the method described herein improves the sorting of various parts into clusters or subsets that enable a statistical analysis/pattern recognition tool to more accurately classify the parts as either non-defective parts or defective parts, thus improving the overall performance of the statistical analysis/pattern recognition tool. The method described herein also provides increased sensitivity to improve parts sorting performance and therefore differentiate between non-defective parts or defective parts. The cluster analysis method also provides the ability to cluster the parts and therefore decreases the amount of variation that needs to be accounted for inside of the good parts, leading to better results. The cluster analysis method also validates the Bias test to prove it is real and valuable, provides the ability to utilize multiple Bias tests, all of which are now validated, and verifies part classification before allowing the part into a training set.

Other additional advantages of the cluster analysis tool and method described herein include providing an ability to sort good parts from bad parts, providing an ability to correlate sorting results to physical properties of "unknown," blind, or new production parts, i.e. the cluster analysis method determines part came from which mold or die and what defect a failed part most likely has. The cluster analysis method also provides improved statistical analysis/pattern recognition tool validation scores such that the statistical analysis/pattern recognition tool does not have to account for the entire process variation across all of the good parts, but only utilizes smaller subsets or clusters. The smaller subsets or clusters enable the statistical analysis/pattern recognition tool to utilize frequencies previously unavailable to the statistical analysis/pattern recognition tool which typically would be frequencies that are from higher quality, easier to pick peaks, making the sort perform better. The cluster analysis method also provides an increased ability to validate newly added parts to training sets and enables multiple new tests to be performed with enhanced sensitivity to smaller defects that would be otherwise more difficult to identify using the statistical analysis/pattern recognition tool alone.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

What is claimed is:

1. A method for classifying an unknown part, said method comprising:
    acquiring a broadband frequency response for a plurality of parts in a training set of parts, the training set of parts including a plurality of non-flawed parts and a plurality of flawed parts;
    performing a statistical analysis on the broadband frequency responses to form a plurality of part subsets, the plurality of part subsets including at least one subset of non-flawed parts and at least one subset of flawed parts; and
    utilizing the plurality of part subsets to form a blended subset of parts, the blended subset of parts being used to classify an unknown part as either a defective part or a non-defective part.

2. The method of claim 1 further comprising:
    stacking the broadband signatures; and
    selecting a plurality of resonant peaks from each broadband signature to perform the statistical analysis.

3. The method of claim 1 further comprising:
    stacking the broadband signatures;
    identifying columns that represent frequency responses that are common among a plurality of broadband signatures; and
    performing the statistical analysis on the identified columns.

4. The method of claim 1 further comprising performing the statistical analysis on the broadband frequency responses to form a plurality of part subsets, the plurality of subsets including a first subset of defective parts and a second subset of defective parts, the first subset including parts having a first flaw type and the second subset including parts having a different second flaw type.

5. The method of claim 1 further comprising performing the statistical analysis on the broadband frequency responses to form a plurality of part subsets, the plurality of subsets including a first subset of defective parts and a second subset of defective parts, the first subset including parts having a crack and the second subset including parts having a dimensional defect.

6. The method of claim 1 further comprising performing the statistical analysis on the broadband frequency responses to form a plurality of part subsets, the plurality of subsets including a first subset of non-defective parts and a second subset of non-defective parts, the first subset including parts having a first physical characteristic and the second subset including parts having a different second physical characteristic.

7. The method of claim 1 further comprising utilizing the plurality of part subsets to form a blended subset of parts, the blended subset of parts being including a plurality of resonant frequencies acquired from a subset of non-defective parts and a plurality of resonant frequencies acquired from a subset of defective parts.

8. The method of claim 1 wherein to form the plurality of subsets, the method further comprises:
forming a first subset to include non-defective parts;
forming a second subset to include non-defective parts;
assigning each non-defective part in the training set a grade based on how far the part is from a center of each of the two non-defective part subsets; and
assigning each non-defective part to either the first subset or the second subset based on the assigned grade.

9. The method of claim 1 wherein to form the plurality of subsets, the method further comprises:
forming a first subset to include defective parts;
forming a second subset to include defective parts;
assigning each defective part in the training set a grade based on how far the part is from a center of each of the two non-defective part subsets; and
assigning each defective part to either the first subset or the second subset based on the assigned grade.

10. The method of claim 1 wherein performing the statistical analysis includes measuring a frequency difference between two resonant responses in each broadband signature.

11. A method of determining whether an unknown part is a flawed part or a non-flawed part, said method comprising:
acquiring a broadband frequency response for each part in a training set of parts, the training set of parts including a plurality of non-flawed parts and a plurality of flawed parts to;
identifying columns that represent frequency responses that are common among the plurality of broadband signatures;
performing a statistical analysis on the identified columns to form a plurality of part subsets; and
utilizing the plurality of part subsets to classify an unknown part as either a defective part or a non-defective part.

12. The method of claim 11 further comprising performing a statistical analysis on the broadband frequency responses to form a plurality of part subsets, the plurality of part subsets including at least one subset of non-flawed parts and at least one subset of flawed parts.

13. The method of claim 11 further comprising utilizing the plurality of part subsets to form a blended subset of parts, the blended subset of parts being used to classify an unknown part as either a defective part or a non-defective part.

14. The method of claim 11 further comprising:
stacking the broadband signatures; and
selecting a plurality of resonant peaks from each broadband signature to perform the statistical analysis.

15. The method of claim 11 wherein forming the plurality of subsets includes forming a first subset of defective parts and a second subset of defective parts, the first subset including parts having a first flaw type and the second subset including parts having a different second flaw type.

16. The method of claim 11 wherein forming the plurality of subsets includes forming a first subset of defective parts and a second subset of defective parts, the first subset including parts having a crack and the second subset including parts having a dimensional defect.

17. The method of claim 11 further comprising utilizing the plurality of part subsets to form a blended subset of parts, the blended subset of parts being including a plurality of resonant frequencies acquired from a subset of non-defective parts and a plurality of resonant frequencies acquired from a subset of defective parts.

18. A cluster analysis tool for determining whether an unknown part is a flawed part or a non-flawed part, said tool comprising:
a ultrasound probe for scanning a training set of parts, the training set of parts including a plurality of non-flawed parts and a plurality of flawed parts to; and
a cluster analysis module coupled to the ultrasound probe, the cluster analysis module configured to:
acquire a broadband frequency response from the ultrasound probe for a plurality of parts in a training set of parts, the training set of parts including a plurality of non-flawed parts and a plurality of flawed parts;
perform a statistical analysis on the broadband frequency responses to form a plurality of part subsets, the plurality of part subsets including at least one subset of non-flawed parts and at least one subset of flawed parts; and
transmit the plurality of part subsets to a statistical analysis tool, the statistical analysis tool forming a blended subset of parts, the blended subset of parts being used to classify an unknown part as either a defective part or a non-defective part.

19. The cluster analysis tool of claim 18, wherein the cluster analysis module is further configured to:
stack the broadband signatures; and
automatically select a plurality of resonant peaks from each broadband signature to perform the statistical analysis.

20. The cluster analysis tool of claim 18, wherein the cluster analysis module is further configured to:
stack the broadband signatures;
identify columns that represent frequency responses that are common among a plurality of broadband signatures; and
perform the statistical analysis on the identified columns.

* * * * *